United States Patent [19] [11] 4,195,024
Archer et al. [45] Mar. 25, 1980

[54] BENZOCYCLOHEPTAPYRANS, COMPOSITIONS, AND METHOD OF TREATMENT

[75] Inventors: Robert A. Archer, Indianapolis, Ind.; Moses W. McMillan, Vicksburg, Mich.

[73] Assignee: Eli Lilly and Company, Indianapolis, Ind.

[21] Appl. No.: 7,116

[22] Filed: Jan. 29, 1979

Related U.S. Application Data

[62] Division of Ser. No. 884,883, Mar. 9, 1978, Pat. No. 4,152,451.

[51] Int. Cl.$^2$ .......................................... C07D 311/94
[52] U.S. Cl. ................................................. 260/345.3
[58] Field of Search ..................................... 260/345.3

[56] References Cited

U.S. PATENT DOCUMENTS

| | | | |
|---|---|---|---|
| 3,507,885 | 4/1970 | Fahrenholtz | 260/345.3 |
| 3,859,306 | 1/1975 | Freedman | 260/333 |
| 3,940,421 | 2/1976 | Razdan et al. | 260/327 TH |
| 3,941,782 | 3/1976 | Harris et al. | 424/267 |
| 3,972,880 | 8/1976 | Harris et al. | 424/267 |
| 4,007,207 | 2/1977 | Winn | 260/345.3 |
| 4,025,630 | 5/1977 | Dren et al. | 424/256 |
| 4,051,152 | 9/1977 | Razdan et al. | 260/345.3 |

Primary Examiner—Nicky Chan
Attorney, Agent, or Firm—Charles W. Ashbrook; Arthur R. Whale

[57] ABSTRACT

Octahydro and hexahydrobenzo[b]cyclohepta[d]pyrans having the general formula

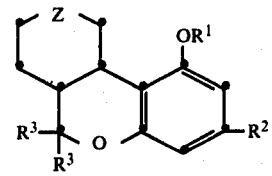

wherein $R^1$ is hydrogen or alkanoyl, $R^2$ is alkyl or alkenyl, $R^3$ is hydrogen or alkyl, and Z is a two carbon alkylene chain which is substituted or unsubstituted and saturated or unsaturated are provided. Pharmaceutical compositions containing such benzocycloheptapyrans, and a method of treating hypertension are disclosed.

17 Claims, No Drawings

BENZOCYCLOHEPTAPYRANS, COMPOSITIONS, AND METHOD OF TREATMENT

This is a division of application Ser. No. 884,883, filed Mar. 9, 1978, now U.S. Pat. No. 4,152,451.

BACKGROUND OF THE INVENTION

The very potent biological activities attributable to compounds structurally related to the active ingredients of *Cannabis sativa* L. has generated a great deal of interest and research during the past several years. Numerous chemical modifications has led to the discovery of extremely potent compounds of the cannabinoid family which are clinically useful. U.S. Pat. Nos. 3,928,598, 3,944,673 and 3,953,603 describe several hexahydrodibenzo[b,d]pyrans which are particularly useful in the treatment of anxiety, pain and depression. Novel methods of preparation of such compounds has been summarized by Archer et al. in *J. Org. Chem.*, 42, 2277 (1977).

While a great deal of synthetic chemistry has been devoted to the modification of the substitution patterns of pharmacologically active dibenzo[b,d]pyrans, very little chemical research has been directed to structural modification of the basic tricyclic nucleus of such compounds. The synthesis of certain B-ring homocannabinoid derivatives, i.e. dibenz[b,d]oxepins, recently has been disclosed by Matsumoto et al., *J. Med. Chem.*, 20, 25(1977) and by Freedman, U.S. Pat. No. 3,859,306. Similarly, benzopyran-type compounds having a 5 or 6-membered C-ring have been described in U.S. Pat. Nos. 2,972,880, 4,051,152, 4,007,207 and 4,025,630.

It is an object of this invention to provide 6,6,7-tricyclic compounds which are structurally similar to dibenzo[b,d]pyrans and which are extremely active pharmacologically while at the same time not causing some of the deleterious side effects often observed with conventional marijuana-like compounds.

SUMMARY OF THE INVENTION

The invention relates to compositions of matter characterized as tricyclic compounds wherein a 6-membered aromatic ring is fused to the b-side of a pyran ring, and a cycloheptane ring is fused to the d-side of such pyran. More particularly, the invention is directed to octahydro and hexahydrobenzo[b]cyclohepta[d]pyrans defined by the general structural formula

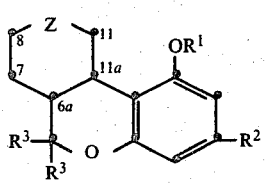

wherein:
$R^1$ is hydrogen or $C_{1-4}$ alkanoyl;
$R^2$ is $C_5-C_{10}$ alkyl or $C_5-C_{10}$ alkenyl;
$R^3$ is hydrogen or methyl; and
Z is selected from the group consisting of

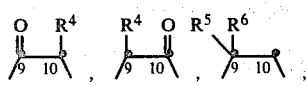

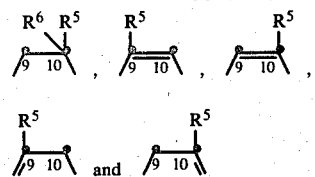

in which:
$R^4$ is hydrogen or $C_1-C_4$ alkoxycarbonyl;
$R^5$ is hydrogen or $C_1-C_4$ alkyl; and
$R^6$ is hydrogen or hydroxy.

A preferred group of compounds are defined by the above formula wherein $R^1$ is hydrogen and $R^3$ is methyl.

Another preferred group of compounds are those according to the above formula wherein Z is selected from

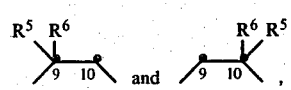

and
$R^5$ is hydrogen or methyl, and
$R^6$ is hydroxy.

A particularly preferred group of benzocycloheptapyrans contemplated by this invention are those of the above formula wherein
$R^1$ is hydrogen,
$R^2$ is alkyl,
$R^3$ is methyl, and
Z is selected from

wherein:
$R^5$ is hydrogen or methyl.

This invention additionally comprehends pharmaceutical formulations comprising as active ingredient at least one of the benzocycloheptapyrans of the above general formula in combination with a suitable diluent or carrier therefor. Such formulations are useful in the treatment of anxiety, pain, depression, glaucoma and hypertension.

A preferred formulation according to this invention comprises a compound of the above general formula wherein
$R^1$ is hydrogen,
$R^2$ is alkyl,
$R^3$ is methyl and
Z is selected from

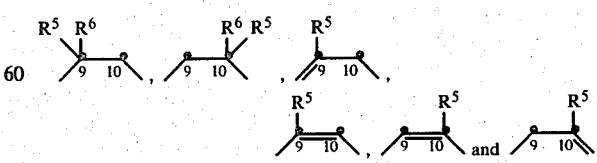

wherein
$R^5$ is hydrogen or methyl and
$R^6$ is hydrogen or hydroxy, in combination with a pharmaceutical carrier therefor.

Yet another embodiment of this invention is a method of treating hypertension which comprises administering to a subject suffering from hypertension and in need of treatment or to a subject suspected of having incipient hypertension an amount sufficient to lower blood pressure of a benzocycloheptapyran having the above general formula.

A preferred method of treatment according to this invention comprises administering a hypotensively effective dose of a compound having the above formula wherein:
- $R^1$ is hydrogen
- $R^2$ is alkyl,
- $R^3$ is methyl, and
- Z is selected from the group consisting of

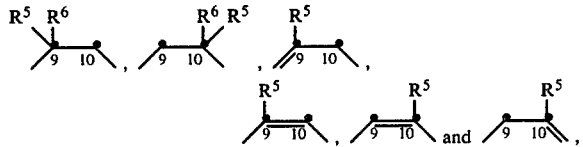

wherein:
$R^5$ is hydrogen or methyl and
$R^6$ is hydrogen or hydroxy.

DETAILED DESCRIPTION OF THE INVENTION

In the above general formula defining the benzocycloheptapyrans provided by this invention, $R^1$ is defined as hydrogen or $C_1$–$C_4$ alkanoyl. The term "$C_1$–$C_4$ alkanoyl" as used herein refers to an acyl residue of a carboxylic acid having from 1 to 4 carbon atoms. Examples of such $C_1$–$C_4$ alkanoyl groups include formyl, acetyl, propionyl, n-butyryl, and isobutyryl.

$R^2$ in the above formula is defined as a $C_5$–$C_{10}$ alkyl group or as a $C_5$–$C_{10}$ alkenyl group. Such terms take on the meaning assigned to them throughout the chemical art relating to dibenzopyrans. Examples of "$C_5$–$C_{10}$ alkyl" groups thus include both straight and branched chain alkyl groups such as n-pentyl, n-hexyl, n-heptyl, 1,1-dimethylheptyl, 1,2-dimethylheptyl, 1-ethyloctyl, 1,1-dimethyloctyl, 1,2,3-trimethylheptyl, 1-propylhexyl, isooctyl, n-decyl, and the like. The term "$C_5$–$C_{10}$ alkenyl" similarly refers to straight and branched alkenyl chains known in the art, examples of which include 2-pentenyl, 3-hexenyl, 5-heptenyl, 1,1-dimethyl-2-heptenyl, 1,2-dimethyl-1-heptenyl, 2,3-dimethyl-2-heptenyl, 1-ethyl-2-octenyl, 2-ethyl-1-heptenyl, 2-decenyl, 1-nonenyl, 1-methyl-1-nonenyl, and related alkenyl groups.

In the above structural definitions for the variable referred to as Z, $R^4$ defines hydrogen or a $C_1$–$C_4$ alkoxycarbonyl moiety. Examples of $C_1$–$C_4$ alkoxycarbonyl groups include methoxycarbonyl, ethoxycarbonyl, isopropoxycarbonyl and tert.-butoxycarbonyl. $R^5$ in the above formulae defines, in addition to hydrogen, a $C_1$–$C_4$ alkyl group such as methyl, ethyl, n-propyl, iso-butyl or the like.

The compounds provided by this invention will be named throughout this disclosure by referring to the following general formula bearing the numbering system as shown:

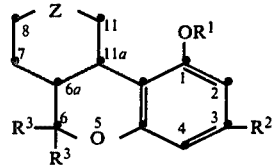

wherein Z has the above-defined meaning, and wherein the two ring carbon atoms defined by Z are numbered in order as 9 and 10 respectively as shown in the above part formulae defining Z. It will be noted by those skilled in the art that since the ring juncture, defined in the above formula as the 6a,11a positions, is totally saturated, several optical isomers are possible because of the asymmetric orientations occurring at those centers. When naming such optical isomers, the following conventions will be observed: when the hydrogen atom attached at the 6a-position is oriented on the side of the molecule opposite to the hydrogen atom attached at the 11a-position, the resulting molecule is said to have a "trans" stereochemical configuration, and is more specifically designated as a 6a,11a-trans racemate. It should be further noted that two optical isomers of the trans configuration are possible. For example, the absolute stereochemical configuration of the 6a-hydrogen atom can be below the plane of the ring, in which case it is referred to as a 6aS-hydrogen atom. Similarly, the 11a-hydrogen atom can be above the plane of the molecule, in which case it is referred to as an 11aS-hydrogen atom. Conversely, the 6a-hydrogen can be above the plane of the ring, and is designated a 6aR hydrogen atom, and the 11a-hydrogen can be oriented below the plane and designated as an 11aR hydrogen atom. The two 6a,11a-trans isomers form a racemic dl or ± pair of isomers. Similarly, both the 6a and 11a hydrogen atoms can be oriented on the same side of the plane of the molecule, in which case the compound is referred to as a "cis" racemate, and more specifically as a 6a,11a-cis racemate. When both the 6a-hydrogen and the 11a-hydrogen atoms are oriented above the plane of the molecule, the compound is more accurately referred to as a 6a,11aS-cis isomer, while if both hydrogen atoms are oriented below the plane of the molecule, the particular isomer is defined as the 6aS,11aR-cis isomer, and the two cis isomers together form a racemic dl or (±) pair.

The absolute stereochemical configuration of the 6a and 11a positions of the benzocycloheptapyrans of this invention will not hereinafter be designated. Rather, it is to be understood that the designation "cis" includes not only the individual mirror image isomers at the 6a and 11a positions in compounds having the above general formula, but also the dl or (±)-mixture of such mirror image cis isomers. Similarly, the term "trans" will include each separate 6aS,11aS isomer and its 6aR,11aR mirror image, as well as the racemic (±)-mixture of such trans isomers. The particular stereochemical configuration occurring at the 6a and 11a positions of the compounds of this invention will be determined by the stereochemical configuration of the starting material from which such compounds are derived, since the stereochemical integrity of the starting material is maintained throughout the synthetic procedures used to prepare the compounds of this invention. Furthermore, since one of the separate optically active isomers may have little or no pharmacological activity, it is preferred to utilize racemic (±) mixtures of isomers as active drugs rather than to prepare and use the corresponding optically active individual isomers. The (±)-6a,11a-trans isomers appear, in general, to be somewhat more active biologically by than the corresponding (±)-6a,11a-cis isomers. It is therefore desirable to prepare and use the (±)-trans-benzo[b]cyclohepta[d]pyrans of this invention. Accordingly such compounds are preferred as active ingredients in the formulations and processes of this invention.

In naming the compounds of this invention, the stereochemical nature of the molecule is first indicated; eg. (±)-trans, (±)-cis, etc. All compounds will be named as benzo[b]cyclohepta[d]pyrans, with the various substituent groups named in order of location on the ring system. As an example, a racemic compound having the above formula wherein $R^1$ is hydrogen, $R^2$ is n-pentyl, $R^3$ is methyl and Z is

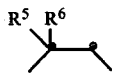

wherein $R^5$ and $R^6$ both are hydrogen, and wherein the hydrogen atoms at the 6a and 11a positions are cis to one another, is named as follows: (±)-6a,11a-cis-1-hydroxy-3-n-pentyl-6,6-dimethyl-6,6a,7,8,9,10,11,11a-octahydrobenzo[b]cyclohepta[d]pyran.

The benzo[b]cyclohepta[d]pyrans provided by this invention are derived from hexahydrodibenzo[b,d]pyran-9-ones. Such starting materials are readily available by various synthetic schemes disclosed in the chemical art. Both (±)-6a,10a-cis and (±)-6a,10a-trans-hexahydrodibenzo[b,d]pyran-9-ones are available by the methods described in U.S. Pat. Nos. 3,953,603 and 3,507,885. Optically active cis and trans pyranone derivatives can be prepared by the methods described by Archer et al. *J. Org. Chem.*, 42, 2277 (1977).

The compounds of this invention are accordingly prepared as follows: a 1-hydroxy-3-alkyl(or 3-alkenyl)-6a,7,8,9,10,10a-hexahydro-6H-dibenzo[b,d]pyran-9-one is reacted with a $C_1$–$C_4$ alkyl ester of diazoacetic acid in the presence of a catalyst such as triethyloxonium tetrafluoroborate or boron trifluoride. The diazoacetic acid ester interacts with the 9-keto group of the dibenzopyranone. The net result of such interaction is the evolution of nitrogen and concomitant ring enlargement to provide a mixture of β-keto esters, which are compounds having the above general formula wherein $R^1$ is hydrogen, $R^2$ is alkyl or alkenyl, $R^3$ is hydrogen or methyl, and Z is selected from the group consisting of

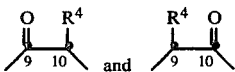

wherein $R^4$ is $C_1$–$C_4$ alkoxycarbonyl. The reaction typically is carried out by mixing the $C_1$–$C_4$ alkyl diazoacetate, the catalyst, either triethyloxonium tetrafluoroborate or boron trifluoride, and the hexahydro-dibenzo[b,d]pyran-9-one in a suitable unreactive solvent such as dichloromethane, diethyl ether, benzene, toluene, or the like. The resulting mixture is stirred at a temperature of about 0° C. to about 20° C. for a period of time ranging from about ten minutes to about three hours. The reactants are conveniently utilized in approximately equimolar quantities; however, an excess of either may be used without materially affecting the yield of benzocycloheptapyran which is formed. Preferably, the alkyl diazoacetate is reacted with about a two to three molar excess of a 1 to 3 molar mixture of the dibenzopyranone and triethyloxonium tetrafluoroborate. The product of such reaction is readily isolated by simply washing the reaction mixture with an aqueous base such as dilute sodium hydroxide or dilute sodium bicarbonate. Separation of the organic layer followed by removal of the solvent by evaporation under reduced pressure then provides, as products of the reaction, a mixture of geometrical isomers at the 9 and 10-positions. In particular, such reaction provides a mixture of 9-oxo-10-alkoxycarbonyl and 9-alkoxycarbonyl-10-oxooctahydrobenzo[b]cyclohepta[d]pyrans. Such mixture is readily separated into its respective components by routine purification procedures such as liquid-solid chromatography, fractional crystallization, high pressure liquid chromatography and the like.

The 9-oxo-10-alkoxycarbonyl and 9-alkoxycarbonyl-10-oxo-octahydrobenzo[b]cyclohepta[d]pyrans thus prepared are useful as pharmacological agents, but are preferably utilized as intermediates in the synthesis of other compounds of this invention. Such compounds can, for example, be hydrolyzed to provide the corresponding β-keto acid, which acid is readily decarboxylated at elevated temperatures. The hydrolysis of the alkoxycarbonyl derivatives can be effected in normal fashion, for instance by reaction with an acid such as hydrochloric acid or a base such as sodium hydroxide. Typically, a 9-oxo-10-alkoxycarbonyl or 9-alkoxycarbonyl-10-oxo-octahydrobenzo[b]cyclohepta[d]pyran is dissolved in an acid such as formic acid, acetic acid, sulfuric acid, hydrochloric acid, or a mixture of any of such acids, and heated to a temperature of about 50° to about 200° C. for a period of time of about one to three hours. The alkoxycarbonyl moiety is converted to a hydroxycarbonyl moiety, which immediately expels carbon dioxide under such reaction conditions to provide the corresponding 9-oxo or 10-oxo-octahydrobenzo[b]cyclohepta[d]pyran. Such compounds have the above general formula wherein $R^1$ is hydrogen, $R^2$ is alkyl or alkenyl, $R^3$ is hydrogen or methyl, and Z is selected from

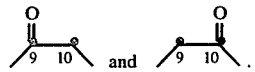

The 9-oxo or 10-oxo derivative thus formed can be isolated by simply extracting the acidic or basic reaction mixture with a suitable water immiscible organic solvent such as diethyl ether, dichloromethane, benzene, or the like. Removal of the organic solvent then provides the corresponding 9-oxo or 10-oxo-octahydrobenzo[b]cyclohepta[d]pyran, which compound can be further purified if desired by standard methods such as crystallization or chromatography.

The 9-oxo and 10-oxo derivatives thus formed, in addition to possessing useful pharmacological activity, are valuable intermediates and can in turn be reduced to provide the 9-hydroxy and 10-hydroxy-octahydrobenzo[b]cyclohepta[d]pyrans of the invention, or alternatively they can be reacted with a $C_1$–$C_4$ alkyl Grignard reagent to afford the corresponding 9-alkyl-9-hydroxy and 10-alkyl-10-hydroxyoctahydrobenzo[b]cyclohepta[d]pyrans of this invention.

The reduction of a 9-oxo or a 10-oxo-octahydrobenzo[b]cyclohepta[d]pyran to afford the corresponding 9-hydroxy or 10-hydroxy derivative can be carried out by reaction with any of a number of routinely used reducing agents. Commonly used reducing agents include organometallics and metal hydrides such as sodium borohydride, diborane, diisoamylborane, lithium aluminum hydride and lithium aluminum trimethoxy hydride. Catalytic hydrogenation can also be employed utilizing catalysts such as palladium and platinum. The reduction reaction, whether chemical or catalytic, generally is carried out in a solvent such as ethanol, diethyl ether, benzene, or the like, and typically is complete within two to about twenty-four hours. As a typical example, a 10-oxo derivative such as 1-hydroxy-3-(2-hexenyl)-10-oxo-6,6a,7,8,9,10,11,11a-octahydrobenzo[b]cyclohepta[d]pyran can be reacted with about a one to ten molar excess of sodium borohydride in a solvent such as ethanol. The reaction is carried out at a temperature of about 20° to 50° C., and is complete within about twelve hours. The product is recovered by simply washing the reaction mixture with an aqueous acid such as dilute hydrochloric acid, separating the organic layer and then removing the solvent therefrom. The product so formed is a racemic mixture of 10-hydroxy benzocycloheptapyran derivatives, wherein the hydroxy group attached to the C-ring is oriented in the α stereochemical position as well as in the β position. Such mixtures can be separated if desired and further purified by standard methods such as chromatography.

Both the 9-hydroxy and the 10-hydroxy-octahydrobenzo[b]cyclohepta[d]pyrans of this invention are valuable pharmacological agents. Such compounds additionally serve as intermediates as described hereinafter.

As previously pointed out, the 9-oxo and 10-oxo-octahydrobenzocycloheptapyrans of this invention can be reacted with $C_1$–$C_4$ alkyl Grignard reagents to provide the corresponding 9-alkyl-9-hydroxy or 10-alkyl-10-hydroxyoctahydrobenzo[b]cyclohepta[d]pyrans of this invention. Such compounds have the above general formula wherein $R^1$ is hydroxy and Z is selected from

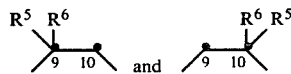

wherein $R^5$ is $C_1$–$C_4$ alkyl and $R^6$ is hydroxy. Commonly used Grignard reagents include methyl magnesium bromide, ethyl magnesium bromide, isobutyl magnesium bromide, and the like. The reaction is carried out according to standard Grignard reaction conditions. For instance, a 9-oxo derivative such as 6a,11a-cis-1-hydroxy-3-n-octyl-9-oxo-6,6a,7,8,9,10,11,11a-octahydrobenzo[b]cyclohepta[d]pyran can be reacted with an excess of a Grignard reagent, such as a two molar excess of n-propyl magnesium bromide. The reaction normally is carried out in an inert solvent such as diethyl ether, generally at a temperature of about 0° to 50° C., and routinely is complete after about ten to twenty hours. The product can be isolated by simply washing the reaction mixture with an aqueous acid, separating the organic layer and then evaporating the reaction solvent therefrom. The product of such reaction is, in the illustration, 6a,11a-cis-1-hydroxy-3-n-octyl-9-hydroxy-9-n-propyl-6,6a,7,8,9,10,11,11a-octahydrobenzo[b]cyclohepta[d]pyran. It should be recognized that such product is a mixture of isomers at the 9-position, since in one case the 9-hydroxy group can be oriented below the plane of the ring (i.e. α) and the 9-alkyl group can be oriented above the plane of the ring (i.e. β), while in another case the 9-hydroxy group can be oriented above and the 9-alkyl group oriented below the plane of the ring. Such mixtures can be separated by chromatography if desired, or can be utilized as a mixture of isomers both pharmacologically and as intermediates in the synthesis of other compounds of the invention.

Any of the 9-alkyl-9-hydroxy and 10-alkyl-10-hydroxy octahydrobenzocycloheptapyrans of this invention can be dehydrated to provide the corresponding 9-alkyl and 10-alkyl hexahydrobenzocycloheptapyrans of this invention, compounds having the above general formula wherein Z is selected from the group consisting of

in which $R^5$ is $C_1$–$C_4$ alkyl.

The dehydration of such 9-alkyl-9-hydroxy or 10-alkyl-10-hydroxy derivatives can be accomplished by reaction with an acid such as sulfuric acid or paratoluenesulfonic acid, generally under essentially anhydrous conditions since water is being formed during the reaction. The reaction preferably is carried out in a solvent which forms an azeotrope with water, thereby allowing the water to be continuously removed from the reaction mixture by distillation of the azeotrope. The reaction typically is carried out in benzene in a flask equipped with a Dean Stark trap for water removal. Other methods available for removing the water which is formed as part of the reaction include the use of molecular sieves. The dehydration reaction generally is carried out at a temperature of about 40° to 80° C. where the azeotrope boils, and is substantially complete within about one to ten hours. The product, a 9-alkyl or 10-alkyl-hexahydrobenzo[b]cyclohepta[d]pyran, is readily isolated by removing any excess acid from the reaction mixture, for instance by washing the mixture with an aqueous base, separating the organic layer and then evaporating the reaction solvent. Further purification can be accomplished if desired by routine methods such as chromatography.

Hexahydrobenzocycloheptapyrans which are unsubstituted in the C ring, ie. compounds having the above formula wherein $R^5$ is hydrogen, can be prepared by dehydration of 9-hydroxy or 10-hydroxy-octahydrobenzocycloheptapyrans. Such compounds preferably are prepared, however, by reacting 9-oxo or 10-oxo-octahydrobenzocycloheptapyrans with paratoluenesulfonylhydrazine to provide the corresponding tosylhydrazone, which when treated with a base such as sodium in ethylene glycol or lithium diisopropylamide in tetrahydrofuran effects elimination of the tosylhydrazone moiety to provide a hexahydrobenzocycloheptapyran.

The hexahydrobenzocycloheptapyrans of this invention are potent pharmacological agents, and also serve as intermediates in the synthesis of the octahydrobenzocycloheptapyrans of this invention which are unsubstituted at the 9 and 10 positions or are substituted with a $C_1$–$C_4$ alkyl group at such positions. For instance, catalytic hydrogenation of a compound such as (±)-6a,11a-trans-1-hydroxy-3-(1,2-dimethylheptyl)-6,6-dimethyl-9-isopropyl-6,6a,7,8,11,11a-hexahydrobenzo[b]cyclohepta[d]pyran by reaction with hydrogen in the presence of a catalyst such as 5 percent palladium on carbon effects hydrogenation of the $\Delta^{9,10}$ double bond to provide (±)-6a,11a-trans-1-hydroxy-3-(1,2-dimethylheptyl)-6,6-dimethyl-9-isopropyl-6,6a,7,8,9,10,11,11a-octahydrobenzo[b]cyclohepta[d]pyran.

It will be noted that all of the above described synthetic reactions are carried out on compounds having a 1-hydroxy group, ie. $R^1$ in the above general formula is hydrogen. Any of the 1-hydroxy compunds heretofore described can be converted to 1-alkanoyloxy derivatives, wherein $R^1$ is $C_1$–$C_4$ alkanoyl, by reaction with an acylating agent. For example, a 10-oxo derivative such as 1-hydroxy-3-isodecyl-10-oxo-6,6a,7,8,9,10,11,11a-octahydrobenzo[b]cyclohepta [d]pyran can be reacted with about an equimolar quantity of an acylating agent such as a $C_1$–$C_4$ alkanoic acid halide or anhydride to provide the corresponding 1-alkanoyloxy-10-oxo derivative. Reduction of such derivative as hereinabove pointed out provides the corresponding 1-alkanoyloxy-10-hydroxy octahydrobenzocycloheptapyran of this invention. The 1-alkanoyloxy compounds provided herein are useful pharmacological agents. When desired, they can be converted to the parent 1-hydroxy derivatives by simple acid or base hydrolysis.

The following list of representative compounds illustrates the scope of benzocycloheptapyrans contemplated by this invention. The listing is by no means inclusive of the various compounds comprehended, but is merely a representation.

(±)-6a,11a-trans-1-hydroxy-3-n-hexyl-9-oxo-10-ethoxycarbonyl-6,6a,7,8,9,10,11,11a-octahydrobenzo[b]cyclohepta[d]pyran;

(±)-6a,11a-cis-1-hydroxy-3-(1,2,3-trimethylhexyl)-6,6-dimethyl-9-methoxycarbonyl-10-oxo-6,6a,7,8,9,10,11,11a-octahydrobenzo[b]cyclohepta[d]pyran;

(−)-6a,11a-trans-1-hydroxy-3-(1-methyl-2-heptenyl)-9-isobutoxycarbonyl-10-oxo-6,6a,7,8,9,10,11,11a-octahydrobenzo[b]cyclohepta[d]pyran;

(±)-6a,11a-trans-1-acetoxy-3-(1,2-dimethyloctyl)-6,6-dimethyl-9-oxo-6,6a,7,8,9,10,11,11a-octahydrobenzo[b]cyclohepta[d]pyran;

(±)-6a,11a-cis-1-formyloxy-3-(2-hexenyl)-10-oxo-6,6a,7,8,9,10,11,11a-octahydrobenzo[b]cyclohepta[d]pyran;

(±)-6a,11a-cis-1-hydroxy-3-n-octyl-6,6-dimethyl-9-ethyl-9-hydroxy-6,6a,7,8,9,10,11,11a-octahydrobenzo[b]cyclohepta[d]pyran;

(−)-6a,11a-trans-1-hydroxy-3-(1,2-dimethylpentyl)-10R-hydroxy-6,6a,7,8,9,10,11,11a-octahydrobenzo[b]cyclohepta[d]pyran;

(±)-6a,11a-trans-1-isobutyroxy-3-n-heptyl-10α-hydroxy-10β-methyl-6,6a,7,8,9,10,11,11a-octahydrobenzo[b]cyclohepta[d]pyran;

(±)-6a,11a-cis-1-hydroxy-3-(1,1-dimethylheptyl)-9-ethyl-6,6a,7,10,11,11a-hexahydrobenzo[b]cyclohepta[d]pyran;

(−)-6a,11a-trans-1-hydroxy-3-(1,2-dimethyl-1-hexenyl)-6,6-dimethyl-9-n-propyl-6,6a,7,8,11,11a-hexahydrobenzo[b]cyclohepta[d]pyran;

(−)-6a,11a-trans-1-acetoxy-3-(1-ethyl-2-methylhexyl)-6,6-dimethyl-10-isopropyl-6,6a,7,8,11,11a-hexahydrobenzo[b]cyclohepta[d]pyran;

(±)-6a,11a-cis-1-propionoxy-3-n-pentyl-6,6,10-trimethyl-6,6a,7,8,9,11a-hexahydrobenzo[b]cyclohepta[d]pyran;

(±)-6a,11a-trans-1-hydroxy-3-(1-ethylheptyl)-6,6-dimethyl-6,6a,7,8,11,11a-hexahydrobenzo[b]cyclohepta[d]pyran;

(±)-6a,11a-cis-1-acetoxy-3-n-octyl-6,6a,7,8,9,10,11,11a-octahydrobenzo[b]cyclohepta[d]pyran; and (±)-6a,11a-trans-1-hydroxy-3-(1,1-dimethyloctyl)-6,6-dimethyl-9-ethyl-6,6a,7,8,11,11a-hexahydrobenzo[b]cyclohepta[d]pyran.

All of the octahydro and hexahydrobenzo[b]cyclohepta[d]pyrans provided by this invention are new chemical compounds having a variety of useful pharmacological activities, and accordingly are useful in treating disorders commonly occuring in humans. A further embodiment of this invention therefore includes pharmaceutical formulations containing at least one of the compounds of this invention in association with one or more pharmaceutically-acceptable diluents, carriers or excipients therefor. If desired, one or more other pharmacologically active drugs can be incorporated into the formulation containing a compound of this invention. The formulations provided by this invention can be administered to mammals, especially humans, for the treatment or control of anxiety, depression, glaucoma and pain. A particularly preferred formulation of this invention is one useful in the treatment of hypertension, and thus comprises a hypotensively effective dose of a compound having the above formula in association with a carrier therefor. Especially preferred formulations useful in the treatment of hypertension comprise a compound having the above formula wherein $R^1$ is hydrogen, $R^2$ is alkyl, $R^3$ is methyl, and Z is selected from the group consisting of

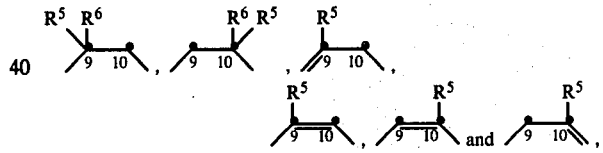

wherein $R^5$ is hydrogen or methyl and $R^6$ is hydrogen or hydroxy, in association with a suitable carrier therefor.

The formulations contemplated by this invention can take on a form which is readily conducive to the particular route of administration desired in each particular case. For oral administration, which is preferred according to this invention, a compound of this invention is admixed with carriers and diluents such as dextrose, lactose, mannitol, calcium silicate, potato starch, microcrystalline cellulose, polyvinylpyrrolidone, cellulose, potassium benzoate, and related excipients. Such formulations can be molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

A particularly preferred formulation useful for treating hypertension in human subjects comprises a compound such as (±)-6a,11a-trans-1-hydroxy-3-(1,1-dimethylheptyl)-6,6,9-trimethyl-6,6a,7,10,11,11a-hexahydrobenzo[b]cyclohepta[d]pyran or (±)-6a,11a-trans-1-hydroxy-3-(1,1-dimethylheptyl)-6,6,9-trimethyl-6,6a,7,8,11,11a-hexahydrobenzo[b]-cyclohepta[d]pyran, or a mixture of such isomers, in the amount of about 100 mcg. to about 250 mcg. in combination with a carrier such as sucrose or starch in the amount of about 300 to about 500 mg. Such formulation can be molded into tablets and administered to a subject suffering from high blood pressure at the rate of from about 1 to about 4 tablets per day or as need by the particular patient.

As already pointed out, the compounds of this invention have a variety of pharmacological utilities. Most of the compounds have demonstrated activity in standard tests designed to show analgesic, anti-depressant and anti-anxiety activity, as well as hypotensive activity. The most potent compounds provided herein appear to be the hexahydro and octahydrobenzocycloheptapyrans of the above general formula wherein $R^5$ is $C_1$–$C_4$ alkyl and $R^6$ is hydrogen or hydroxy. Especially preferred compounds are the 9-alkyl and the 10-alkyl-hexahydrobenzocycloheptapyrans, particularly those wherein the 9-alkyl or 10-alkyl group is methyl. Even though such compounds are preferred because of their biological properties, all of the compounds provided herein are useful biologically. For example, (±)-6a,11a-trans-1-hydroxy-3-(1,1-dimethylheptyl)-6,6-dimethyl-9-ethoxycarbonyl-10-oxo-6,6a,7,8,9,10,11,11a-octahydrobenzo[b]cyclohepta[d]pyran had a minimum effective dose (MED) of only 2.5 mg./kg. p.o. when analyzed in the standard mouse activity assay. Similarly, when (±)-6a,11a-trans-B 1-hydroxy-3-(1,1-dimethylheptyl)-6,6-dimethyl-9-oxo-B 6,6a,7,8,9,10,11,11a-octahydrobenzo[b]cyclohepta[d]pyran was tested in the septal lesion rat assay, it demonstrated an MED of 5.0 mg./kg. p.o. When (±)-6a,11a-trans-1-hydroxy-3-(1,1-dimethylheptyl)-6,6-dimethyl-10α-hydroxy-6,6a,7,8,9,10,11,11a-octahydrobenzo[b]cyclohepta[d]pyran was assayed for analgesic activity in the mouse writhing test, it demonstrated an $ED_{50}$ p.o. of only 0.2 mg./kg. When tested for their ability to reduce the blood pressure of rabbits, (±)-6a,11a-trans-1-hydroxy-3-(1,1-dimethylheptyl)-6,6,10β-trimethyl-10α-hydroxy-6,6a,7,8,9,10,11,11a-octahydrobenzo[b]cyclohepta[d]pyran had an MED of 16 mcg./kg. i.v., while a mixture of (±)-6a,11a-trans-1-hydroxy-3-(1,1-dimethylheptyl)-6,6,9-trimethyl-6,6a,7,10,11,11a-hexahydrobenzo[b]cyclohepta[d]pyran and the 6,6a,7,8,11,11a-hexahydro derivative had an MED of only 2 mcg./kg. when administered intravenously.

As can readily be seen from the foregoing discussion of biological activity, the compounds of this invention are useful in the treatment of hypertension, anxiety, depression, pain, glaucoma and related maladies. The compounds can thus be used to treat animals and humans alike suffering from one or more of such conditions. A further embodiment of this invention is a method of treating hypertension in mammals comprising administering a hypotensive dose of a hypotensively active compound of this invention to a subject suffering from hypertension and in need of treatment or to a subject suspected of developing hypertension and in need of prophylactic treatment. An especially preferred method of treating hypertension according to this invention comprises administering a compound of this invention having the above general formula wherein $R^1$ is hydrogen, $R^2$ is alkyl, $R^3$ is methyl and Z is selected from the group consisting of

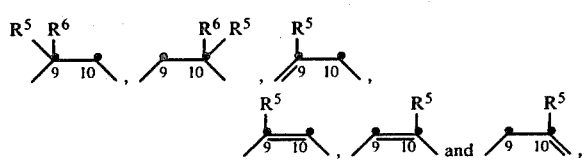

wherein $R^5$ is hydrogen or methyl and $R^6$ is hydrogen or hydroxy.

The hypotensively active benzocycloheptapyran derivatives of this invention can be administered by any of a number of routes, including the oral, subcutaneous, intramuscular and intravenous routes. Typical dosages useful for the treatment of humans will of course vary depending upon the particular hypertension condition being treated, but typically will range from about 0.1 to about 10 mcg./kg. of subject body weight. Daily dosages commonly utilized when treating hypertension, for example, will range from about 1 to about 500 mcg. for a patient weighing about 50 to about 75 kg. A commonly used dose will be in the amount of about 50 mcg. to about 100 mcg.

The preparation of the benzocycloheptapyran compounds comprehended by this invention is more fully described in the following examples. It is of course to be understood, however, that the examples are illustrative of the compounds embraced by the invention and of methods commonly employed in their preparation and are not to be construed as limiting the invention to any of the particular compounds or methods specifically described.

EXAMPLE 1

(±)-6a,11a-trans-1-Hydroxy-3-(1,1-dimethylheptyl)-6,6-dimethyl-9-oxo-10α-ethoxycarbonyl-6,6a,7,8,9,10,11,11a-octahydrobenzo[b]cyclohepta[d]pyran A solution of 12.97 g. of (±)-6a,10a-trans-1-hydroxy-3-(1,1-dimethylheptyl)-6,6-dimethyl-6a,7,8,9,10,10a-hexahydrodibenzo[b,d]pyran-9-one in 175 ml. of dichloromethane was stirred under nitrogen and cooled in an ice bath. To the cold reaction mixture was added 14 g. of triethyloxonium tetrafluoroborate followed by the addition of 7.7 ml. of ethyldiazoacetate. The reaction mixture then was stirred at about 5° C. for one hour and then diluted with 250 ml. of 5 percent aqueous sodium bicarbonate solution. The organic layer was separated and the aqueous layer was extracted with fresh dichloromethane. The organic layers were combined, dried and the solvent was removed therefrom by evaporation under reduced pressure to provide 16.2 g. of the product as a red oil. The oil thus formed was applied to the chromatographic column packed with silica gel and the column was eluted with 2 percent ethyl acetate in dichloromethane. The fractions shown by thin layer chromatographic analysis to contain the desired product were combined and the solvent was removed therefrom by evaporation under reduced pressure thus affording 5.36 g. of the desired product as a clear oil. The clear oil was crystallized from hexane and dichloromethane to afford (±)-6a,11a-trans-1-hydroxy-3-(1,1-dimethylheptyl)-6,6-dimethyl-9-oxo-10α-ethoxycarbonyl -6,6a,7,8,9,10,11,11a-octahydrobenzo[b]cyclohepta[d]pyran, m.p. 101°–102° C.

IR (CHCl$_3$): 5.78μ (C=O ester); 5.86μ (C=O ketone), H$^1$ NMR (CDCl$_3$): δ 7.82 (s, 1H); δ 4.34 (q, 2H); δ 1.34 (t, 3H); mass spec. m/e 458 (M$^+$);

Analysis Calc. For C$_{28}$H$_{42}$O$_5$—Theory: C, 73.33; H, 9.23. Found: C, 73.10; H, 9.44.

EXAMPLE 2

(±)-6a,11a-trans-1-Hydroxy-3-(1,1-dimethylheptyl)-6,6-dimethyl-9-ethoxycarbonyl-10-oxo-6,6a,7,8,9,10,11,11a-octahydrobenzo[b]cyclohepta[d]-pyran Further chromatographic separation of the crude product obtained as described in Example 1 provided fractions containing the desired compound as demonstrated by thin layer chromatogrpahic analysis. The appropriate fractions were combined and the solvent was removed therefrom by evaporation under reduced pressure to provide 2.74 g. of the desired product as a light yellow oil. The oil thus formed was crystallized from hexane to provide (±)-6a,11a-trans-1-hydroxy-3-(1,1-dimethylheptyl)-6,6-dimethyl-9-ethoxycarbonyl-10-oxo-6,6a,7,8,9,10,11,11a-octahydrobenzo[b]cyclohepta[d]pyran, m.p. 121°–124° C.

IR (CHCl$_3$): 5.67μ (C=O ester); 5.90μ (C=O ketone); H$^1$ NMR (CDCl$_3$): δ 4.22 (q, 2H); δ 1.26 (t, 3H); mass spec. m/e 458 (M$^+$);

Anaylsis Calc. for C$_{28}$H$_{42}$O$_5$—Theory: C, 73.33; H, 9.23; O, 17.44. Found: C, 73.07; H, 9.05; O, 17.34.

EXAMPLE 3

(±)-6a,11a-trans-1-Hydroxy-3-(1,1-dimethylheptyl)-6,6-dimethyl-9-oxo-10β-ethoxycarbonyl-6,6a,7,8,9,10,11,11a-octahydrobenzo[d]cyclohepta[d]-pyran A solution of 1.0 g. of (±)-6a,11a-trans-1-hydroxy-3-(1,1-dimethylheptyl)-6,6-dimethyl-9-oxo-10α-ethoxycarbonyl-6,6a,7,8,9,10,11,11a-octahydrobenzo[b]cyclohepta[d]pyran in 25 ml. of pyridine was stored at 25° C. for 48 hours. The reaction mixture was diluted with water and with 100 ml. of ethyl acetate and the aqueous mixture then was washed twice with 200 ml. portions of 1 N hydrochloric acid, once with 100 ml. of water, and once with 50 ml. of brine solution. The remaining organic layer was dried and the solvent was removed by evaporation under reduced pressure to provide 900 mg. of the product as a yellow oil. The oil thus formed was crystallized from hexane to provide (±)-6a,11a-trans-1-hydroxy-3-(1,1-dimethylheptyl)-6,6-dimethyl-9-oxo-10β-ethoxycarbonyl-6,6a,7,8,9,10,11,11a-octahydrobenzo[b]cyclohepta[d]pyran, m.p. 96°–98.5° C.

IR (CHCl$_3$): 5.78μ (C=O ester); 5.86μ (C=O ketone); H$^1$ NMR (CDCl$_3$): δ 4.95 (s, 1H); δ 1.23 (t, 3H); mass spec. m/e 458 (M$^+$);

Analysis Calc for C$_{28}$H$_{42}$O$_5$—Theory: C, 73.33; H, 9.23. Found: C, 73.59; H, 9.29.

EXAMPLE 4

(±)-6a,11a-trans-1-Hydroxy-3-(1,1-dimethylheptyl)-6,6-dimethyl-9-oxo-6,6a,7,8,9,10,11,11a-octahydrobenzo[b]cyclohepta[d]pyran A solution of 6.0 g. of a mixture containing (±)-6a,11a-trans-1-hydroxy-3-(1,1,-dimethylheptyl)-6,6-dimethyl-9-oxo-10α-ethoxycarbonyl-6,6a,7,8,9,10,11,11a-octahydrobenzo[b]cyclohepta[d]pyran and the corresponding 10β-ethoxycarbonyl derivative dissolved in 800 ml. of acetic acid containing 320 ml. of concentrated hydrochloric acid and 100 ml. of water was stirred and heated at reflux for 2 hours. The reaction mixture then was cooled to room temperature and diluted with 1 liter of water. The aqueous reaction mixture was extracted three times with 200 ml. portions of dichloromethane. The organic extracts were combined, washed with water, with 5 percent sodium bicarbonate solution, with brine, and dried. Removal of the solvent by evaporation under reduced pressure afforded 4.8 g. of a greenish oil. The oil thus formed was applied to a chromatographic column packed with silica gel and eluted with 3 percent ethyl acetate and benzene. Fractions shown by thin layer chromatographic analysis to contain a single product were combined and the solvent was removed therefrom by evaporation to afford 2 g. of a clear oil. The oil was crystallized from hexane to provide (±)-6a,11a-trans-1-hydroxy-3-(1,1-dimethylheptyl)-6,6-dimethyl-9-oxo-6,6a,7,8,9,10,11,11a-octahydrobenzo[b]cyclohepta[d]pyran as white crystals, m.p. 102.5°–104.5° C.

IR (CHCl$_3$): 5.90μ (C=O); H$^1$ NMR (CDCl$_3$); δ 5.35 (s, 1H); δ 1.17 (s, 6H); δ 0.80 (t, 3H); mass spec. m/e 386 (M$^+$);

Analysis Calc. for C$_{25}$H$_{38}$O$_3$—Theory: C, 77.68; H, 9.91. Found: C, 77.62; H, 9.88.

EXAMPLE 5

(±)-6a,11a-trans-1-Hydroxy-3-(1,1-dimethylheptyl)-6,6-dimethyl-10-oxo-6,6a,7,8,9,10,11,11a-octahydrobenzo[b]cyclohepta[d]pyran Following the general procedure set forth in Example 4, a solution of 3.3 g. of (±)-6a,11a-trans-1-hydroxy-3-(1,1-dimethylheptyl)-6,6-dimethyl-9-ethoxycarbonyl-10-oxo-6,6a,7,8,9,10,11,11a-octahydrobenzo[b]cyclohepta[d]pyran in acetic acid, water and concentrated hydrochloric acid was heated to reflux and stirred for 2 hours. The product was isolated and purified by chromatography and crystallization from methylcyclopropane and dichloromethane to afford (±)-6a,11a-trans-1-hydroxy-3-(1,1-dimethylheptyl)-6,6-dimethyl-10-oxo-6,6a,7,8,9,10,11,11a-octahydrobenzo[b]cyclohepta[d]pyran as white crystals, m.p. 81.5°–83.5° C.

IR (CHCl$_3$): 5.95μ (C=O); H$^1$ NMR (CDCl$_3$); δ 5.92 (s, 1H); δ 1.17 (s, 6H); δ 0.82 (t, 3H); mass spec. m/e 386 (M$^+$);

Analysis Calc. for C$_{25}$H$_{38}$O$_3$—Theory: C, 77.68; H, 9.91. Found: C, 77.56; H, 10.18.

EXAMPLE 6

(±)-6a,11a-trans-1,9α-Dihydroxy-3-(1,1-dimethylheptyl)-6,6-dimethyl-6,6a,7,8,9,10,11,11a-octahydrobenzo[b]cyclohepta[d]pyran A solution of 1.005 g. of (±)-6a,11a-trans-1-hydroxy-3-(1,1-dimethylheptyl)-6,6-dimethyl-9-oxo-6,6a,7,8,9,10,11,11a-octahydrobenzo[b]cyclohepta[d]pyran dissolved in 50 ml. of ethyl alcohol was added in one portion to a stirred suspension of 0.6 g. of sodium borohydride in 30 ml. of ethyl alcohol. The reaction mixture was stirred at room temperature for 12 hours and then added to 125 ml. of a cold solution of 0.1 N hydrochloric acid. The organic layer was then separated and the aqueous layer was extracted with diethyl ether. The organic layers were combined, washed with water, and dried. Removal of the solvent by evaporation under reduced pressure provided a white foam. The foam thus formed was applied to a chromatographic column packed with silica gel and eluted with 5 percent acetonitrile and dichloromethane. The fraction shown by thin layer chromatographic analysis to contain the major component were combined and the solvent was removed therefrom by evaporation to provide the product as a white foam. The product was shown to consist of a mixture of (±)-6a,11a-trans-1,9α-dihydroxy-(and 1,9β-dihydroxy)-3-(1,1-dimethylheptyl)-6,6-dimethyl-6,6a,7,8,9,10,11,11a-octahydrobenzo[b]cyclohepta[d]pyran.

UV (CH$_3$OH) λ$_{max}$]08 (ε=43860); mass spec. m/e 388 (M+);

Analysis Calc. for C$_{25}$H$_{40}$O$_3$—Theory: C, 77.27; H, 10.38. Found: C, 77.18; H, 10.15.

EXAMPLE 7

(±)-6a,11a-trans-1,10α-Dihydroxy-3-(1,1-dimethylheptyl)-6,6-dimethyl-6,6a,7,8,9,10,11,11a-octahydrobenzo[b]cyclohepta[d]pyran Following the same general procedure set forth in Example 6, a solution of 1.335 g. of (±)-6a,10a-trans-1-hydroxy-3-(1,1-dimethylheptyl)-6,6-dimethyl-10-oxo-6,6a,7,8,9,10,11,11a-octahydrobenzo[b]cyclohepta[d]pyran in 75 ml. of ethyl alcohol was reduced by reaction with 800 mg. of sodium borohydride in 35 ml. of ethyl alcohol. The product was isolated as described in Example 6 to provide 1.242 g. of a crude oil. Chromatography of the oil so formed over a column packed with silica gel, eluting with 2 percent acetonitrile and dichloromethane, afforded 468 mg. of an oil which when crystallized from hexane gave white crystalline (±)-6a,11a-trans-1,10α-dihydroxy-3-(1,1-dimethylheptyl)-6,6-dimethyl-6,6a,7,8,9,10,11,11a-octahydrobenzo[b]cyclohepta[d]pyran, m.p. 109°-110° C.

UV (CH$_3$OH): λ$_{max}$ 209, 273 (ε=52217; 1124); H$^1$ NMR (CDCl$_3$): δ 7.26 (s, 1H); δ 2.60 (s, 1H); δ 1.20 (s, 6H); δ 0.83 (t, 3H); mass spec. m/e 388 (M+);

Analysis Calc. for C$_{25}$H$_{40}$O$_3$—Theory: C, 77.27; H, 10.38. Found: C, 77.09; H, 10.28.

EXAMPLE 8

Further chromatographic separation of the crude product prepared in Example 7 afforded fractions which when combined and concentrated to dryness under reduced pressure gave 1.013 g. of an oil. The oil was crystallized from hexane to afford white crystalline (±)-6a,11a-trans-1,10β-dihydroxy-3-(1,1-dimethylheptyl)-6,6-dimethyl-6,6a,7,8,9,10,11,11a-octahydrobenzo[b]cyclohepta[d]pyran, m.p. 146.5°-147.5° C.

UV (CH$_3$OH): λ$_{max}$ 208,273 (ε=50016; 1091); H$^1$ NMR (CDCl$_3$): δ 6.12 (s, 1H); δ 1.18 (s, 6H); δ 0.83 (t, 3H); mass spec. m/e 388 (M+);

Analysis Calc. for C$_{25}$H$_{40}$O$_3$—Theory: C, 77.26; H, 10.38. Found: C, 77.20; H, 10.41.

EXAMPLE 9

(±)-6a,11a-trans-1,10α-Dihydroxy-3-(1,1-dimethylheptyl)-6,6,10β-trimethyl-6,6a,7,8,9,10,11,11a-octahydrobenzo[b]cyclohepta[d]pyran A solution of 1.051 g. of (±)-6a,11a-trans-1-hydroxy-3-(1,1-dimethylheptyl)-6,6-dimethyl-10-oxo-6,6a,7,8,9,10,11,11a-octahydrobenzo[b]cyclohepta[d]pyran in 40 ml. of dry diethyl ether was added dropwise over 10 minutes to a stirred refluxing solution of 10 ml. of 3 molar methyl magnesium bromide in 10 ml. of dry diethyl ether. Following complete addition, the reaction mixture was stirred and heated at reflux for 18 hours and then cooled to room temperature and diluted with 100 ml. of 0.1 N hydrochloric acid solution which had been chilled to 0° C. in an ice bath. The acidity of the reaction mixture was adjusted to pH 5 by the dropwise addition of 1 N hydrochloric acid. The organic layer then was separated and the aqueous layer was extracted with 50 ml. of fresh diethyl ether. The organic portions then were combined and washed twice with 100 ml. portions of water, once with a 50 ml. portion of brine, and dried. Removal of the solvent by evaporation under reduced pressure afforded 804 mg. of a white foam. The foam was applied to a chromatographic column packed with silica gel and eluted with a gradient solvent starting at 2 percent acetonitrile in dichloromethane and ending with 3 percent acetonitrile in dichloromethane. Fractions shown by thin layer chromatographic analysis to contain one componet were combined and the solvent was removed therefrom by evaporation under reduced pressure to afford 649 mg. of a white foam. The foam was crystallized from hexane to afford (±)-6a,11a-trans-1,10α-dihydroxy-3-(1,1-dimethylheptyl)-6,6,10β-trimethyl-6,6a,7,8,9,10,11,11a-octahydrobenzo[b]cyclohepta[d]pyran, m.p. 113°-115° C.

UV (CH$_3$OH) λ$_{max}$ 208 (ε=50187); H$^1$ NMR (CDCl$_3$): δ 1.20 (s, 6H); δ 0.83 (t, 3H); mass spec. m/e 402 (M+);

Analysis Calc. for C$_{26}$H$_{42}$O$_3$—Theory: C, 77.56; H, 10.52. Found: C, 77.62; H, 10.33.

EXAMPLE 10

Further chromatographic separation of the crude product obtained as described in Example 9 provided fractions which were shown by thin layer chromatographic analysis to contain a single component which was different than the product of Example 9. Such fractions were combined and the solvent was removed therefrom to provide 56 mg. (±) dl-6a,11a-trans-1,10β-dihydroxy-3-(1,1-dimethylheptyl)-6,6,10α-trimethyl-6,6a,7,8,9,10,11,11a-octahydrobenzo[b]cyclohepta[d]pyran as a white solid.

H$^1$ NMR (CDCl$_3$): δ 4.95 (s, 1H); δ 1.19 (s, 6H); δ 0.83 (t, 3H); mass spec. Calc. for C$_{26}$H$_{42}$O$_3$ 402.31338; found 402.31316.

EXAMPLES 11–12

(±)-6a-11-a-trans-1,9α-Dihydroxy-3-(1,1-dimethylheptyl)-6,6,9β-trimethyl-6,6a,7,8,9,10,11,11a-octahydrobenzo[b]cyclohepta[d]pyran and
(±)-6a,11a-trans-1,9β-dihydroxy-3-(1,1-dimethylheptyl)-6,6,9α-trimethyl-6,6a,7,8,9,10,11,11a-octahydrobenzo[b]cyclohepta[d]pyran To a stirred refluxing solution of 9.7 ml. of a three molar solution of methyl magnesium bromide in 20 ml. of diethyl ether was added over 10 minutes a solution of 957 mg. of (±)-6a,11a-trans-1-hydroxy-3-(1,1-dimethylheptyl)-6,6-dimethyl-9-oxo-6,6a,7,8,9,10,11,11a-octahydrobenzo[b]cyclohepta[d]pyran in 40 ml. of diethyl ether. The reaction mixture was stirred and heated at reflux for 12 hours and then cooled to room temperature and poured into 50 ml. of ice water. One normal hydrochloric acid solution was added to the cold aqueous reaction mixture to adjust the pH of the solution to 7. The organic layer then was separated and the aqueous layer was extracted with 50 ml. of fresh diethyl ether. The organic phases were combined, washed once with 100 ml. of water and once with 50 ml. of brine and dried. Evaporation of the solvent under reduced pressure provided 943 mg. of a clear oil. The oil thus formed was crystallized from acetonitrile and dichloromethane to provide as a white crystalline product (±)-6a,11a-trans-1,9α-dihydroxy-3-(1,1-dimethylheptyl)-6,6,9β-trimethyl-6,6a,7,8,9,10,11,11a-octahydrobenzo[b]cyclohepta[d]pyran, m.p. 155.5°–157° C.

UV (CH$_3$OH) $\lambda_{max}$ 209 ($\epsilon$=44012); H$^1$ NMR (CDCl$_3$): δ 4.91 (s, 1H); δ 1.17 (s, 6H); δ 0.82 (t, 3H); mass spec. m/e 402 (M$^+$);

Analysis Calc. for C$_{26}$H$_{42}$O$_3$—Theory: C, 77.56; H, 10.52. Found: C, 77.29; H, 10.28.

The filtrate from the above-described crystallization was concentrated to dryness by evaporation of the solvent under reduced pressure and the residue thus formed was applied to a chromatographic column packed with silica gel and eluted with a 5 percent solution of methanol in dichloromethane. Fractions shown by thin layer chromatography to contain one component were combined and the solvent was removed therefrom by evaporation to provide 50 mg. of a white solid which was shown to be (±)-6a,11a-trans-1,9β-dihydroxy-3-(1,1-dimethylheptyl)-6,6,9α-trimethyl-6,6a,7,8,9,10,11,11a-octahydrobenzo[b]cyclohepta[d]pyran.

UV (CH$_3$OH) $\lambda_{max}$ 209 ($\epsilon$=44012); H$^1$ NMR (CDCl$_3$): δ 6.04 (s, 1H); δ 1.18 (s, 6H); δ 0.84 (t, 3H);

Mass spec. Calc. for C$_{26}$H$_{42}$O$_3$—Theory: 402.31338. Found: 402.31316.

EXAMPLE 13

(±)-6a,11a-trans-1-Hydroxy-3-(1,1-dimethylheptyl)-6,6,9-trimethyl-6,6a,7,8,11,11a-hexahydrobenzo[b]cyclohepta[d]pyran and
(±)-6a,11a-trans-1-hydroxy-3-(1,1-dimethylheptyl)-6,6,9-trimethyl-6,6a,7,10,11,11a-hexahydrobenzo[b]cyclohepta[d]pyran A solution containing 100 mg. of a 50:50 mixture of (±)-6a,11a-trans-1,9α-dihydroxy-3-(1,1-dimethylheptyl)-6,6,9β-trimethyl-6,6a,7,8,9,10,11,11a-octahydrobenzo[b]cyclohepta[d]pyran and the corresponding 9β-hydroxy-9α-methyl compound dissolved in 100 ml. of benzene containing 100 mg. of p-toluenesulfonic acid was stirred and heated at reflux in a flask equipped with a Dean Stark trap for water removal. The reaction mixture was heated at reflux for 1 hour and then cooled to room temperature and washed twice with 50 ml. portions of water, once with 25 ml. of 5 percent aqueous sodium bicarbonate, and once with 25 ml. of brine. The organic layer was separated and dried, and the solvent was removed therefrom by evaporation under reduced pressure to provide the crude product as a brownish oil. The oil was purified by chromatography over a column packed with fluorosil and eluted with a 2 percent solution of diethyl ether in petroleum ether. Fractions shown by thin layer chromatographic analysis to contain the major component were combined and the solvent was removed to provide a mixture of (±)-6a,11a-trans-1-hydroxy-3-(1,1-dimethylheptyl)-6,6,9-trimethyl-6,6a,7,8,11,11a-hexahydrobenzo[b]cyclohepta[d]pyran and the corresponding 6,6a,7,10,11,11a-hexahydrobenzo[b]cyclohepta[d]pyran.

H$^1$ NMR (CDCl$_3$): δ 4.9 (s, 1H); δ 1.7 (s, 3H);
mass spec. Calc. for C$_{26}$H$_{40}$O$_2$—Theory: 384.30281. Found: 384.30181.

EXAMPLE 14

(±)-6a,11a-trans-1-Hydroxy-3-(1,1-dimethylheptyl)-6,6,10-trimethyl-6,6a,7,8,11,11a-hexahydrobenzo[b]cyclohepta[d]pyran and
(±)-6a,11a-trans-1-hydroxy-3-(1,1-dimethylheptyl)-6,6,10-trimethyl-6,6a,7,8,9,11a-hexahydrobenzo[b]cyclohepta[d]pyran Following the general procedure set forth in Example 13, 500 mg. of a mixture of (±)-6a,11a-trans-1,10α-dihydroxy-3-(1,1-dimethylheptyl)-6,6,10β-trimethyl-6,6a,7,8,9,10,11,11a-octahydrobenzo[b]cyclohepta[d]pyran and the corresponding 10β-hydroxy-10α-methyl compound was reacted with 50 mg. of p-toluenesulfonic acid in 75 ml. of benzene. The reaction mixture was worked up in the normal fashion and the crude product was purified by chromatography over fluorosil, eluting with 2 percent diethyl ether in petroleum ether. The appropriate fractions were combined and concentrated to dryness to afford a product identified as a mixture of (±)-6a,11a-trans-1-hydroxy-3-(1,1-dimethylheptyl)-6,6,10-trimethyl-6,6a,7,8,11,11a-hexahydrobenzo[b]cyclohepta[d]pyran and the corresponding 6,6a,7,8,9,11a-hexahydrobenzo[b]cyclohepta[d]pyran.

H$^1$ NMR (CDCl$_3$): δ 4.9 (s, 1H); δ 2.4 (s, 3H);
Mass spec. Calc. for C$_{26}$H$_{40}$O$_2$—Theory: 384.30281. Found: 384.30234.

EXAMPLE 15

(±)-6a,11a-trans-1-Hydroxy-3-(1,1-dimethylheptyl)-6,6-dimethyl-6,6a,7,10,11,11a-hexahydrobenzo[b]cyclohepta[d]pyran and
(±)-6a,11a-trans-1-hydroxy-3-(1,1-dimethylheptyl)-6,6-dimethyl-6,6a,7,8,11,11a-hexahydrobenzo[b]cyclohepta[d]pyran.

A solution of 707 mg. of (±)-6a,11a-trans-1-hydroxy-3-(1,1-dimethylheptyl)-6,6-dimethyl-9-oxo-6,6a,7,8,9,10,11,11a-octahydrobenzo[b]cyclohepta[d]pyran in 25 ml. of methanol containing 341 mg. of para-toluenesulfonylhydrazide was stirred at room temperature for 4 hours. Removal of the solvent by evaporation under reduced pressure provided 1.05 g. of (±)-6a,11a-trans-1-hydroxy-3-(1,1-dimethylheptyl)-6,6-dimethyl-9-(p-toluenesulfonylhydrazino)-6,6a,7,8,9,10,11,11a-octahydrobenzo[b]cyclohepta[d]pyran. A solution of the latter compound in 50 ml. of tetrahydrofuran was added dropwise over thirty minutes to a cold stirred solution of 0.77 ml. of diisopropylamine in 10 ml. of tetrahydrofuran containing 3.43 ml. of a 1.0 molar solution of n-butyl lithium in hexane. Following complete addition, the reaction mixture was warmed to room temperature and stirred for three hours. The reaction mixture next was diluted by the addition of 20 g. of ice and it was then poured into 100 ml. of fifty percent diethyl ether in water. The ethereal layer was separated, washed with water and with brine, and dried. Removal of the solvent by evaporation under reduced pressure provided 500 mg. of an oil. The oil was purified by high pressure liquid chromatography, eluting with dichloromethane, to afford 306 mg. of (±)-6a,10a-trans-1-hydroxy-3-(1,1-dimethylheptyl)-6,6-dimethyl-6,6a,7,10,11,11a-hexahydrobenzo[b]cyclohepta[d]pyran and the corresponding $\Delta^{9,10}$-isomer.

Mass spec. Calc. for C$_{25}$H$_{38}$O$_2$—Theory: 370.28668. Found: 370.287.

EXAMPLE 16

A formulation suitable for the treatment of hypertension according to this invention may have the following composition:

| | |
|---|---|
| (±)-trans-1-hydroxy-3-(1,1-dimethyl heptyl)-6,6,9-trimethyl-6,6a,7,10,11,11a-hexahydrobenzo-[b]cyclohepta[d]pyran | 50 mcg. |
| (±)-trans-1-hydroxy-3-(1,1-dimethyl-heptyl)-6,6,9-trimethyl-6,6a,7,8,11,-11a-hexahydrobenzo-[b]cyclohepta[d]pyran | 50 mcg. |
| polyoxyethylenesorbitan monooleate | 50 mcg. |
| starch powder | 250 mg. |

The above ingredients should be thoroughly mixed and can be placed in an empty gelatin capsule. Such capsules may be administered orally to a human from 1 to about 4 times a day for the control of high blood pressure.

We claim:

1. A compound having the formula

[structure]

wherein:

$R^1$ is hydrogen or $C_1$–$C_4$ alkanoyl;
$R^2$ is $C_5$–$C_{10}$ alkyl or $C_5$–$C_{10}$ alkenyl;
$R^3$ is hydrogen or methyl; and
Z is selected from the group consisting of

[structures]

wherein:

$R^4$ is hydrogen or $C_1$–$C_4$ alkoxycarbonyl;
$R^5$ is hydrogen or $C_1$–$C_4$ alkyl; and
$R^6$ is hydrogen or hydroxy.

2. The compound of claim 1 wherein Z is

[structures]

3. The compound of claim 1 wherein Z is

[structures]

4. The compound of claim 1 wherein Z is selected from

[structures]

5. The compound of claim 1 wherein $R^1$ is hydrogen.

6. The compound according to claim 5 wherein $R^2$ is $C_5$–$C_{10}$ alkyl.

7. The compound according to claim 5 wherein $R^3$ is methyl.

8. The compound according to claim 7 wherein Z is selected from

[structures]

9. The compound according to claim 8 wherein $R^5$ is hydrogen.

10. The compound according to claim 8 wherein $R^5$ is $C_1$–$C_4$ alkyl.

11. The compound according to claim 10 wherein $R^5$ is methyl.

12. The compound according to claim 11 wherein Z

[structures]

13. The compound according to claim 12, said compound being the 6a,11a-trans isomer.

14. The compound according to claim 13, said compound being (±)-6a,11a-trans-1-hydroxy-3-(1,1-dimethylheptyl)-6,6,9-trimethyl-6,6a,7,10,11,11a-hexahydrobenzo[b]cyclohepta[d]pyran.

15. The compound according to claim 13, said compound being (±)-6a,11a-trans-1-hydroxy-3-(1,1-dimethylheptyl)-6,6,9-trimethyl-6,6a,7,8,11,11a-hexahydrobenzo[b]cyclohepta[d]pyran.

16. The compound according to claim 13, said compound being (±)-6a,11a-trans-1-hydroxy-3-(1,2-dimethylheptyl)-6,6,9-trimethyl-6,6a,7,10,11,11a-hexahydrobenzo[b]cyclohepta[d]pyran.

17. The compound according to claim 13, said compound being (±)-6a,11a-trans-1-hydroxy-3-(1,2-dimethylheptyl)-6,6,9-trimethyl-6,6a,7,8,11,11a-hexahydrobenzo[b]cyclohepta[d]pyran.

* * * * *